(12) United States Patent
Junker et al.

(10) Patent No.: US 8,011,249 B2
(45) Date of Patent: Sep. 6, 2011

(54) STEAM GENERATOR NONDESTRUCTIVE EXAMINATION METHOD

(75) Inventors: Warren R. Junker, Monroeville, PA (US); John P. Lareau, Granby, CT (US)

(73) Assignee: Westinghouse Electric Company LLC, Cranberry Township, PA (US)

( * ) Notice: Subject to any disclaimer, the term of this patent is extended or adjusted under 35 U.S.C. 154(b) by 0 days.

(21) Appl. No.: 12/629,112

(22) Filed: Dec. 2, 2009

(65) Prior Publication Data
US 2010/0071470 A1 Mar. 25, 2010

Related U.S. Application Data

(62) Division of application No. 11/562,782, filed on Nov. 22, 2006, now Pat. No. 7,647,829.

(60) Provisional application No. 60/740,061, filed on Nov. 28, 2005.

(51) Int. Cl.
*G01N 29/04* (2006.01)
(52) U.S. Cl. ............... 73/623; 73/592; 73/600
(58) Field of Classification Search ......... 73/622, 73/623, 600, 602, 592; 376/252, 316
See application file for complete search history.

(56) References Cited

U.S. PATENT DOCUMENTS

| | | | |
|---|---|---|---|
| 3,455,121 A * | 7/1969 | Brisson et al. ............ 62/268 |
| 4,162,635 A | 7/1979 | Triplett et al. | |
| 4,218,923 A | 8/1980 | Triplett et al. | |
| 4,244,749 A | 1/1981 | Sachs et al. | |
| 4,595,419 A | 6/1986 | Patenaude | |
| 4,597,294 A * | 7/1986 | Brill et al. ............... 73/623 |
| 4,699,665 A * | 10/1987 | Scharton et al. ........... 134/1 |
| 4,738,737 A * | 4/1988 | Runde et al. ............. 156/91 |
| 4,856,337 A * | 8/1989 | Metala et al. ............ 73/601 |
| 4,955,235 A * | 9/1990 | Metala et al. ............ 73/601 |
| 5,058,432 A | 10/1991 | Morkun et al. | |
| 5,104,611 A * | 4/1992 | Woods et al. ............ 376/203 |
| 5,215,706 A | 6/1993 | Cross et al. | |
| 5,734,588 A | 3/1998 | Rose et al. | |
| 5,767,410 A | 6/1998 | Lareau et al. | |
| 5,982,839 A | 11/1999 | Hatley | |
| 6,148,672 A | 11/2000 | Cawley et al. | |
| 6,487,922 B1 * | 12/2002 | Bauer et al. ............ 73/865.8 |
| 6,595,061 B2 | 7/2003 | Gorman et al. | |
| 7,064,472 B2 * | 6/2006 | Pelrine et al. ........... 310/324 |
| 7,362,032 B2 * | 4/2008 | Pelrine et al. ........... 310/309 |

OTHER PUBLICATIONS

Wilcox et al., "Mode and Transducer Selection for Long Range Lamb Wave Inspection", Journal of Intelligent Material Systems and Structures, vol. 12—Aug. 2001, pp. 553-565.
Rose, Joseph L., "A Baseline and Vision of Ultrasonic Guided Wave Inspection Potential", Journal of Pressure Vessel Technology, Aug. 2002, vol. 124, pp. 273-282.

* cited by examiner

*Primary Examiner* — J M Saint Surin

(57) ABSTRACT

A method of examining a steam generator heat exchange tube from the outside surface employing ultrasonic nondestructive inspection techniques. An ultrasonic transducer contacts the outside surface of the tube and transmits a pseudo helical Lamb wave into the wall of the tube chosen to have a mode that does not significantly interact with water in the tube. The reflected waves are then analyzed for changes in modes to identify defects in the wall of the tube.

3 Claims, 3 Drawing Sheets

STEAM GENERATOR NONDESTRUCTIVE EXAMINATION METHOD

CROSS REFERENCE TO RELATED APPLICATIONS

This application is a divisional application of application Ser. No. 11/562,782, filed Nov. 22, 2006 and is related to and claims priority from provisional application Ser. No. 60/740,061, filed Nov. 28, 2005 entitled Wear Scar Characterization For The Nuclear Industry.

BACKGROUND OF THE INVENTION

1. Field of the Invention

This invention pertains generally to the nondestructive examination of metal tubes and more particularly to the nondestructive examination of heat exchanger tubes from the secondary side of a steam generator to characterize wear scars on the heat exchanger tubes that may warrant further examination from the primary side.

2. Description of the Prior Art

Steam generators used in nuclear reactor power plants are very large heat exchangers where heat from a primary fluid heated by a nuclear reactor is transferred to a secondary fluid which is converted into steam and used to drive a turbine generator. Steam generators are housed inside a tall generally cylindrical steel shell. A large numbered of U-shaped heat exchanger tubes are enclosed in the shell and have their ends inserted in holes formed in a horizontal tube sheet or plate near the bottom of the steel shell. The tubes are used to convey the primary fluid which has been heated in the nuclear reactor. The secondary fluid or feed water used to generate the steam is introduced into the steam generator in such a manner that the secondary fluid flows around the outside of the heated tubes thereby converting much of the secondary fluid into steam which is allowed to exit the steam generator through an outlet nozzle at the top of the steel shell.

In the past, steam generator tubing in nuclear plants have been exposed to extreme operating conditions and were susceptible to stress corrosion cracking, mechanical wear, thinning and pitting. To address this susceptibility, a number of techniques have been developed to inspect steam generator tubing for degradation prior to tubing failure in order to prevent forced outages. Steam generator tubing has been most commonly inspected using a variety of eddy current methods, most involving probes which were inserted into the tubes from the underside of the tube sheet on the primary side of the steam generator. The probes were inserted through a steam generated manway in the lower hemispherical inlet and outlet sides of the generator below the tube sheet and into the tube sheet whereby the corresponding tubes were mapped by inserting the probes up through the tubes.

Though highly accurate, the eddy current method of inspecting steam generator tubing is relatively slow and expensive, in that it is time consuming, requires drainage of the primary side of the generator and increases the exposure of inspection personnel to radiation by opening up the primary side of the steam generator.

While there have been a number of attempts to use ultrasonic techniques for inspecting steam generator tubing, as explained in U.S. Pat. No. 5,767,410, in general, most of these techniques used the Lamb ultrasonic wave method of inspection to supplement the eddy current method. A main advantage of the Lamb wave method is that it is not a "spot" technique for tubing inspection as are the eddy current methods. Using Lamb waves, a defect can be detected at relatively long distances from the probe. The range of an ultrasonic Lamb wave probe depends on the wave mode, the information about the defect sought, and the probe design used. The ultrasonic Lamb wave method is attractive because the attenuation of Lamb waves in a metal medium is exceptionally low. The Lamb waves can propagate for a relatively long distance without losing much energy. Lamb waves of a typical amplitude can still be readily detected after traveling a distance of about 10 meters. Another important feature is that Lamb wave propagation is not sensitive to relatively smooth changes in the tubing diameter or the tube bend, such as expansion transition, dents and U-bends.

With the replacement of the majority of the older nuclear steam generators with new designs utilizing thermally treated I690 many utilities are opting for longer intervals between tubing inspections, thus not having to open the primary side of the steam generator during outages. This has significant cost savings. The maintenance that is performed on the steam generator during intervals between primary side inspections takes place from the secondary side of the unit. Typically, this involves looking for loose parts and/or cleaning of deposits from the secondary side. If a loose part is found, it is removed. However, on occasions where the part is in intimate contact with the tube, wear may have occurred on the tube. Often, the visual inspection techniques available to characterize the wear are incapable of determining the difference between superficial removal of the deposits on the tube and significant wear. The narrow tube lanes, i.e., within the order of 3 mm clearance, makes it extremely difficult to characterize the depth and severity of a wear scar to an extent that would provide sufficient confidence that a wear mark would not develop into a leak. Thus, when a wear scar is identified on the secondary side the primary side of the steam generator must be opened and eddy current or ultrasonic techniques applied from the inside surface of the tube to characterize the depth of the wear scars. This clearly involves significant expense. What is needed is a technique for determining the significance of the wear scars from the secondary side eliminating the need to open the primary side of the steam generator.

SUMMARY OF THE INVENTION

The foregoing need is satisfied by the method of this invention for non-destructively examining the walls of heat exchanger tubes from the secondary side of a steam generator while the primary side is water solid. The method includes the steps of contacting the outer surface of a wall of the tube with an ultrasonic transducer that transmits a helical like Lamb wave into the wall and analyzing reflected or altered Lamb waves for defects within the tube wall. The ultrasonic transducer can be positioned on the tube being examined at the tube sheet, on the U-bend or on an intermediate location and the helical like Lamb wave can be transmitted unidirectionally or bidirectionally in a pseudo helical pattern along the length of the tube. The focus of the helical Lamb wave travels a first axial distance while making a 360° rotation around the wall of the tube and preferably the ultrasonic transducer is moved axially along the outer surface of the tube a distance equal to at least the first axial distance while transmitting intermittent Lamb waves. The ultrasonic transducer or a second ultrasonic transducer receives reflected or altered ultrasonic waves in an interval between transmissions of the outgoing helical Lamb waves. In another preferred embodiment the ultrasonic transducer is moved axially in increments and the helical Lamb wave is transmitted substantially at each increment.

In still another preferred embodiment the method includes the step of tuning the frequency of the Lamb wave to sweep across a given band of frequencies to focus on different points in the tube wall. The given band of frequencies preferably extends substantially on either side of a primary frequency that may range between 700 KHz and 2 MHz. The frequency band extends approximately five percent and more preferably one percent on either side of the primary frequency.

In one preferred embodiment the outside of the steam generator heat exchanger tubes are visually examined with a small remote camera that can be manipulated between the heat exchanger tubes in the tube bundle. The location and shape of wear scars are recorded and mapped. A laboratory mockup of a steam generator heat exchanger tube filled with water is constructed with a wear scar that corresponds in location and form to that recorded during the visual inspection. A transducer is coupled to the tube mockup at a location remote from the wear scar and moved relative to the tube mockup while the transducer's frequency and the angle of introduction of the ultrasonic signal is varied until a mode is identified that results in a response that is least affected by the water in the tube and best characterizes the wear scar. The transducer is then applied to the outside of the steam generator tube on which the wear scar was originally, visually detected, preferably biased against the tube and operated in the mode identified in the laboratory to characterize the wear scar. The Lamb wave mode for the various mode scar signatures or shapes are then recorded in a library that can be searched when additional wear scars are encountered so that the identified modes can be used for subsequently detected wear scars of the same class.

In still another embodiment the ultrasonic transducer is either a phased array transducer or an EMAT transducer. Preferably the transducer has a biasing mechanism that can leverage off of adjacent tubes to pressure the transducer against the tube being interrogated to maximize the coupling of the ultrasonic signal through the tube/transducer interface. The biasing mechanism may, for example, be a spring pack or an inflatable bladder.

BRIEF DESCRIPTION OF THE DRAWINGS

A further understanding of the invention can be gained from the following description of the preferred embodiments when read in conjunction with the accompanying drawings in which.

DESCRIPTION OF THE PREFERRED EMBODIMENTS

Figure 1:
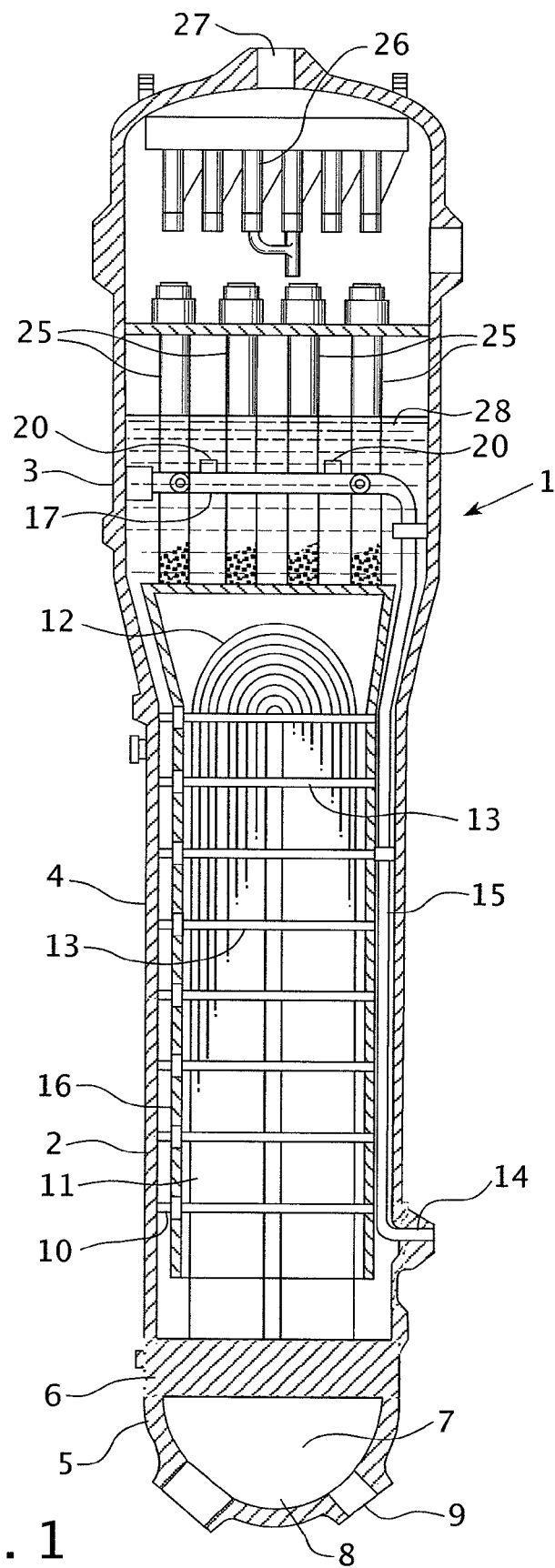
FIG. 1 is a cross sectional view of a U-tube steam generator for which this invention can be applied.

As stated above, steam generators used in nuclear reactor power plants are very large heat exchangers in which heat from a primary fluid heated by the nuclear reactor is transferred to a secondary fluid "water" which is converted into steam and used to drive a turbine generator. FIG. 1 illustrates such a steam generator. The steam generator 1 comprises a steel shell 2 of generally cylindrical shape having a large upper steam section 3, a middle section 4, and a lower channel head section 5. A horizontal circular tube sheet or plate 6 is attached to the steel shell 2 and separates the lower channel head section 5 from the middle section 4. A vertical dividing plate 7 in the channel head section 5 is attached to the tube sheet 6 and at its bottom to the channel head 5 and serves to divide the channel head section 5 into a primary fluid inlet plenum 8 and a primary fluid outlet plenum (not shown). A pair of man holes 9 provide access to the channel head section 5, as required.

The cylindrical middle section 4 of the steam generator 1 contains large numbers of U-shaped heat exchanger tubes 11 which are assembled into a tube bundle 12 and attached at their ends to openings in the tube sheet 6. A plurality of vertically spaced, horizontal support plates or baffles 13 have openings therein similar to those in the tube sheet 6 to hold the tubes in a proper vertical alignment. Large openings are also provided in the support plates or baffles 13 to allow the secondary fluid and steam to flow upward through the tube bundle 12 of the steam generator 1.

Secondary fluid or feedwater is introduced into a feedwater inlet nozzle 14 located in the lower portion of the middle section 4 of the steel shell 2 above the tube sheet 6. Feedwater inlet nozzle 14 is connected to a feedwater riser pipe 15 positioned between the inside surface of the steel shell 2 and the outside of the cylindrical tube bundle wrapper 16 that is spaced inwardly from the inside surface of the steel shell 2 by spacers 10. Feedwater riser pipe 15 extends up the length of the middle section 4 and into the enlarged upper steam section 3 where it is connected to a circular feedwater distribution ring 17 provided with a plurality of spray nozzles 20, which spray the secondary fluid or feedwater into a recirculating pool 28 which receives the drain water from the steam separators 25,26. The steam separators 25,26 respectively form the primary and secondary dryers for separating moisture from the steam before the steam is conveyed out the steam flow outlet nozzle 27 to the turbine generators. By introducing the feedwater in the recirculating pool 28, the cooled incoming feedwater is allowed to mix with the hot recirculating water and the resulting rise in feedwater temperature greatly reduces the thermal shock on the system and its components.

Although not shown in FIG. 1 the steel shell 2 also includes manhole covers in the lower part of the middle section 4 through which maintenance access can be obtained. Maintenance on the secondary side mainly involves removing sludge from the tube sheet that had been deposited over time as a result of the change of phase from water to steam. The heat exchanger tubes in the first generation of nuclear U-tube steam generator were highly susceptible to stress corrosion cracking. The integrity of these tubes had to be inspected at practically every outage and were nondestructively tested by inserting eddy currents detectors through the manholes 9 and into the inlet channel 8 and through the tube sheet 6 to the individual tubes 11. The eddy current detectors were then mapped around and along the tubes to locate flaws. If individual tubes were determined to be defective they were then either sleeved or plugged to avoid the possibility of primary coolant leaking into the secondary system, to maintain the primary coolant barrier to minimize exposure to radiation. The eddy current inspection process was extremely time consuming and expensive. It necessitated the drainage of the primary coolant loop so the inlet and outlet channels of the steam generator could be accessed and exposed the maintenance personnel to increased amounts of radiation.

With the replacement of the majority of the older nuclear steam generators with the new designs utilizing thermally treated I690 many utilities are opting for longer intervals between tubing inspections. The longer time period between inspections meant that it was not necessary to open the primary side of the steam generator during every outage. This has significant cost savings. The maintenance that is performed on the steam generators during intervals between eddy current inspections takes place from the secondary side of unit. Typically, this involves looking for loose parts and/or the cleaning of deposits from the secondary side. As mentioned above, if a loose part is found, it is removed. However, on occasions where the part is in intimate contact with the tube, wear may have occurred on the tube. Often, the visual inspection techniques available to characterize the wear are able to detect the wear scars and identify their location and shape but are incapable of determining the difference between a superficial removal of the deposits on the tube and significant wear. The consequence is that the primary side of the steam generator must be opened and eddy current or ultrasonic techniques applied from the inside surface of the tube to characterized the depth of the wear scars. This clearly involves significant expense. What is needed is a technique for determining the significance of the wear scars from the secondary side, eliminating the need to open the primary side of the steam generator. However, interrogation of the wear scars to determine their significance is complicated by the narrow clearance in the lanes in between the tubes in the tube bundle 12. A typical tube lane clearance is in the order of slightly more than 3 mm. This invention satisfies that need by providing an ultrasonic technique that can be applied to the outside of the steam generator heat exchanger tubes while the tubes are filled with water.

When ultrasonic waves are introduced into structures where a dimension of the structure is comparable to the wave length of the sound, modes of propagation different from those in the bulk material can occur. In the case of tubing, the dimension that can be comparable to the wave length is the wall thickness. Some of the modes have minimal interaction with material in contact with the tube surface while other modes interact strongly. For this application, the inspection element will be placed on the outside of the tube while the inside of the tube is filled with water. A mode, therefore, that has minimal interaction with the presence of the water is the most desirable. Further, the modes of propagation will depend upon the wall thickness and the frequency of the ultrasonic wave. The speed of propagation will be a function of the mode and the frequency.

Figure 2:
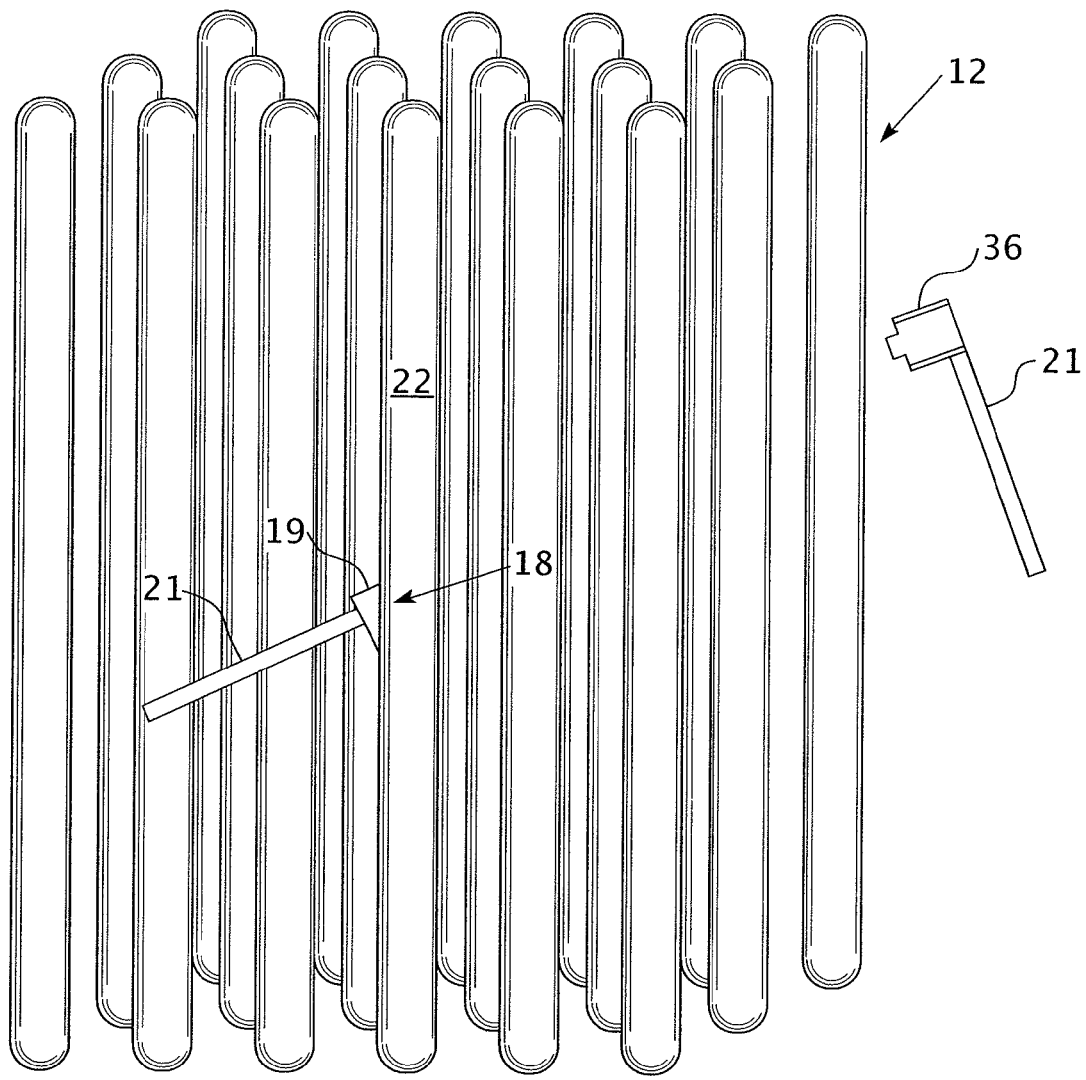
FIG. 2 is a schematic representation of a steam generator tube bundle showing the delivery arms and the camera and transducer assemblies being applied to a steam generator heat exchanger tube.

FIG. 2 provides a schematic representation of a steam generator tube bundle 12 showing a piezoelectric transducer 18 mounted on a coupling wedge 19 and brought into contact with the outside of a heat exchanger tube 22 by a delivery arm 21. The piezoelectric transducer 18 is employed to excite the desired mode. The shape of the wedge and the frequency of the ultrasonic wave generated by the transducer 18 determine the mode of propagation. One limitation of this technique is that the wall thickness of the tubing is not constant. Tubing manufacturers allow a variation in wall thickness. Since the desired mode of propagation depends on the frequency, wall thickness, and the wedge dimensions, an arbitrary wedge may or may not be optimal for a specific tube. To compensate for this the transducer 18 of this invention is a phase array transducer. The apparent angle of incidence is varied by appropriate pulse forming to assure that the energy from the transducer couples into the desired mode. With the proper mode and coupling wedge it is possible that the wave can propagate over considerable distances such that a transducer assembly placed near the tube sheet could characterize wear to above the top support plate 13 (shown in FIG. 1). Thus, an observed wear location need not be directly accessible to the ultrasonic transducer assembly. Further, while the ultrasonic energy is injected into the tube at one azimuthal location and propagates along the axis of the tube the energy spreads as it propagates forming a spiral, pseudo helical or helical like pattern. Thus, a wear scar on the opposite side of the tube (180° away) is still detectable. Since the energy propagation is spiral like it is desirable to move the transducer assembly axially over the length of complete wave rotation to ensure complete coverage over the entire circumference of the tube.

Figure 3:
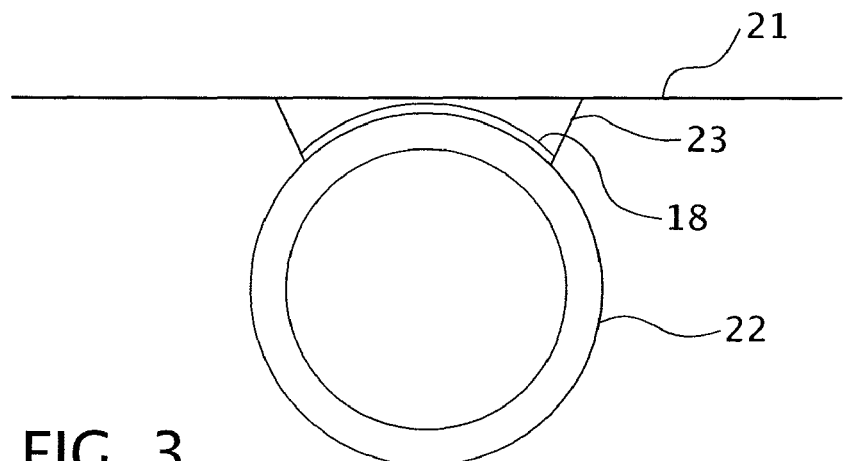
FIG. 3 is a planned view of a section of a steam generator tube showing the transducer contacting a portion of the tube circumference on one side and being bonded to a delivery arm on the other side.

FIG. 3 shows a planned view of a cross section of the tube 22 that has an ultrasonic piezoelectric transducer 18 in direct contract. The transducer 18 is held in place by a bonding material 23, which attaches the transducer to a delivery arm 21. In the preferred embodiment it is desirable that the profile of the combination of the transducer and the delivery arm be equal to 3 mm or less so that the transducer can be inserted within the tube lanes.

Figure 4:
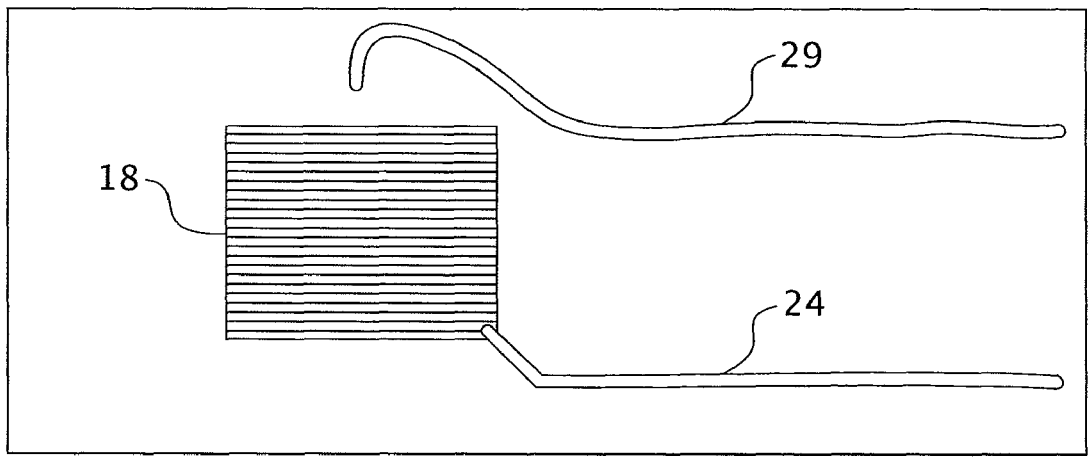
FIG. 4 is a view of a transducer mounted on a delivery arm showing the signal cable and couplant line that supplies a coupling medium between the transducer and the tube at their interface.

FIG. 4 illustrates the transducer assembly that includes a piezoelectric ultrasonic transducer 18 having a signal cable 24 that transmits an intermittent burst of ultrasonic energy and receives reflected signals in between the ultrasonic transmissions. A couplant line 29 is also provided for injecting a couplant such as water between the transducer 18 and the tube 22 to assist the transmission of the ultrasonic energy into the surface of the tube.

Figure 5:
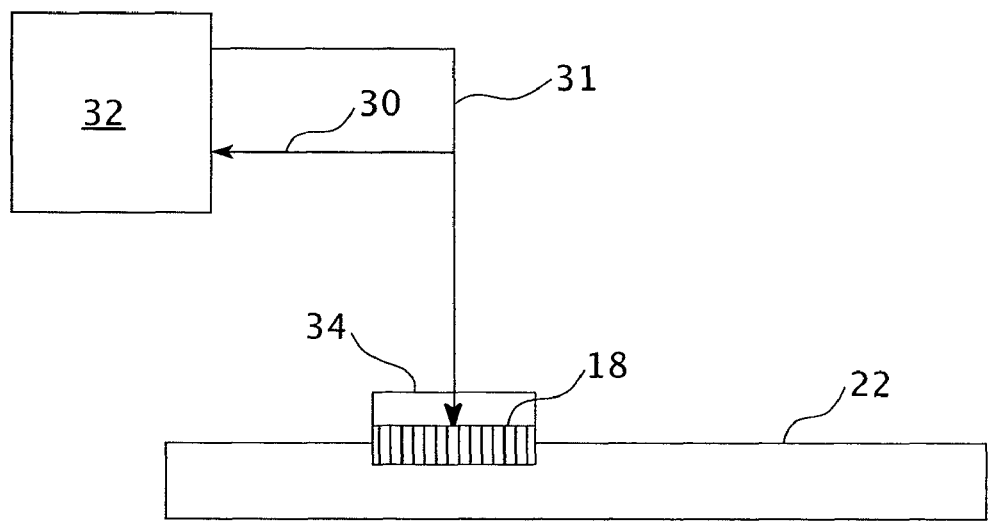
FIG. 5 is a block representation of the transducer system of this invention.

FIG. 5 schematically illustrates an inspection system having a transducer 18 coupled to a pipe 22. The transducer 18 receives a pulse output 31 from an InterSpec Dos with a programmable tone burst generator 32. A reflected signal 30 is received between bursts and is analyzed in the InterSpec Dos 32 to characterize the reflected signal.

The methodology of this invention relies on the interaction of the propagating mode with the region of the tube where the wear scar has occurred. A significant wear scar represents a significant change in wall thickness and therefore a change in mode will occur when the wave propagates through a wear scar region having a significant change in wall thickness. Energy from the interrogating wave will be "reflected" by the presence of the wear scar back to the transducer assembly to be detected. The absence of the reflected response indicates that the wear is not significant and therefore does not require repair. For wear that occurs in the vicinity of the tube sheet it is possible to use two ultrasonic sensors, located above and below the wear operating in a pitch-catch mode. In this scenario, energy is transmitted from one transducer and received by the second transducer located on the opposite side of the wear scar. The presence of the wear scar is detected by a change in the arrival time and presence of additional or missing modes of propagation resulting from a change in wall thickness associated with the wear scar as the energy passes through. For both the reflected and transmitted modes of detection, analysis of the frequency content and arrival time of the response provides information as to the potential through wall extent of the wear scar.

The invention thus contemplates one or two transducer assemblies comprising the piezoelectric phase array transducers, the appropriately designed wedge and the electronics to excite the transducer and to detect and interpret the received energy. The received response is then processed using commercially available algorithms to separate the arrival of the energy associated with the various modes (frequency) and the arrival time. Such commercially available algorithms, e.g., wavelet transforms, can be found in products such as LABVIEW from National Instrument Corp. (ni.com) and UTTEST from FBS Inc. From derived data the depth of the wear scar can be estimated.

The invention also includes the means to bring the transducer assembly into contact with the appropriate tube within the steam generator and then to move the transducer assembly axially along the tube to assure complete interrogation of the entire circumference of the tube. The means for bringing the transducer assembly into contact with the appropriate tube can be the delivery arm 21 shown in FIG. 2 or it can be any other remote positioning mechanism such as a robotic vehicle or arm. Contact with the heat exchanger tube to be interrogated can be enhanced by leveraging off of adjacent tubes using an inflatable bladder or spring pack 34 as is shown in FIG. 5. While the transducer assembly described here is a piezoelectric phase array mounted on a wedge, it can also take the form of an EMAT transducer (Electro Magnetic Air Coupled Transducer), either in a single mode or as a phase array. Preferably, to interrogate the tube at various locations along its elongated length it is desirable that the transducer be scanned through a range of frequencies centered around a primary frequency which preferably is between 700 KHz and 2 MHz. The range should typically span five percent on either side of the primary frequency and more preferably one percent on either side of the primary frequency. Additionally, it should be appreciated that the ultrasonic transducer can be positioned in the U-bend region and the ultrasonic signal transmitted in opposites directions along the length of the tube to inspect the entire tube from one location.

In one preferred embodiment the outside of the steam generator heat exchanger tubes are visually examined with a small remote camera, such as the camera 36 shown in FIG. 2. The camera can be manipulated between the heat exchanger tubes in the tube bundle 12 for a thorough investigation of the outside surface of each of the heat exchanger tubes. The location and shape of the wear scars are recorded and mapped. A laboratory mockup of a steam generator heat exchanger tube filled with water is then constructed with a wear scar that desirably corresponds in location and form to that recorded during the visual inspection. An ultrasonic transducer is then coupled to the tube mockup at a location remote from the wear scar and moved relative to the tube mockup while the transducer's frequency and the angle of introduction of the ultrasonic signal is varied until a mode is identified that results in a response that is least affected by the water in the tube and best characterizes the wear scar's penetration through the tube wall. By being least affected by the water in the tube means that the ultrasonic signal is least attenuated by not being coupled into the water at the tube wall/water interface. The mode being determined is defined by the angle of introduction and the frequency of the ultrasonic signal. In still another embodiment identification of the preferred mode is determined by experimentally varying the transducer's frequency and the angle of introduction of the ultrasonic signal directly on the steam generator heat exchanger tube exhibiting the wear scar. Once the proper mode is selected by the foregoing experimental technique the ultrasonic transducer can be applied directly to the steam generator heat exchanger tubes that the visual inspection identified as having wear scars. The Lamb wave mode for the various wear scar signatures or shapes are then recorded in a library that can be searched when additional wear scars are encountered so that the identified modes can be used for subsequently detected wear scars of the same class, i.e. wear scars of the same or similar shape on the same size tube.

While specific embodiments of the invention have been described in detail, it will be appreciated by those skilled in the art that various modifications and alternatives to those details could be developed in light of the overall teachings of the disclosure. Accordingly, the particular embodiments disclosed are meant to be illustrative only and not limiting as to the scope of the invention, which is to be given the full breadth of the appended claims and any and all equivalents thereof.

What is claimed is:

1. An ultrasonic transducer having a profile that configured to navigate a clearance in lanes between heat exchange tubes in a secondary side of a nuclear steam generator wherein the clearance is approximately 3 mm, including a biasing mechanism that configured to leverage off of adjacent heat exchange tubes to positively press the ultrasonic transducer into firm contact with a heat exchange tube to be interrogated for wear scars.

2. The ultrasonic transducer of claim 1 wherein the biasing mechanism is a spring pack.

3. The ultrasonic transducer of claim 1 wherein the biasing mechanism is an inflatable bladder.

* * * * *